United States Patent
Kurumatani et al.

[11] Patent Number: 5,632,776
[45] Date of Patent: May 27, 1997

[54] IMPLANTATION MATERIALS

[75] Inventors: Hajimu Kurumatani; Hiroshi Kataoka; Kyoko Yamada, all of Kanagawa, Japan

[73] Assignee: Toray Industries, Inc., Japan

[21] Appl. No.: 290,171

[22] Filed: Aug. 15, 1994

Related U.S. Application Data

[63] Continuation of Ser. No. 867,678, filed as PCT/JP91/01609, Nov. 22, 1991, published as WO92/09312, Jun. 11, 1992, abandoned.

[30] Foreign Application Priority Data

Nov. 22, 1990 [JP] Japan ............... 2-318768

[51] Int. Cl.$^6$ ............... A61F 2/04; A61F 2/06
[52] U.S. Cl. ............... 623/11; 623/1; 623/12
[58] Field of Search ............... 623/1, 11, 12, 623/66; 600/36; 606/194, 195, 151–158

[56] References Cited

U.S. PATENT DOCUMENTS

| | | | |
|---|---|---|---|
| 4,229,838 | 10/1980 | Mano | 623/1 |
| 4,661,530 | 4/1987 | Gogolewski et al. | 623/1 |
| 4,695,280 | 9/1987 | Watanabe et al. | 623/1 |
| 4,784,659 | 11/1988 | Fleckenstein et al. | 623/1 |
| 4,822,361 | 4/1989 | Okita et al. | 623/12 |
| 4,879,135 | 11/1989 | Greco et al. | 623/1 |
| 4,902,289 | 2/1990 | Yannas | 623/1 |
| 4,902,290 | 2/1990 | Fleckenstein et al. | 623/1 |
| 4,960,423 | 10/1990 | Smith | 623/1 |
| 4,979,959 | 12/1990 | Guire | 623/1 |
| 5,100,422 | 3/1992 | Berguer et al. | 623/1 |

FOREIGN PATENT DOCUMENTS

| | | | |
|---|---|---|---|
| 0382158 | 8/1990 | European Pat. Off. | 623/1 |
| 1173811 | 12/1969 | United Kingdom | 623/1 |
| 2092894 | 8/1982 | United Kingdom | 623/1 |
| 8002641 | 12/1980 | WIPO | 623/1 |
| 8905830 | 6/1989 | WIPO | 623/1 |

Primary Examiner—Debra S. Brittingham
Attorney, Agent, or Firm—Austin R. Miller

[57] ABSTRACT

The present invention is implantation materials comprising an anti-thrombogenic material contained in the surface in contact with blood, of a porous substrate with its voids filled with denatured albumin or a biodegradable polyester. Since they are excellent in anti-thrombogenic property and allow the positive introduction of cells into the implantation materials, they can prevent thrombogenesis for long periods of time. Especially even if they are used as artificial small diameter blood vessels of less than 6 mm in inner diameter, they show excellent patency.

15 Claims, 1 Drawing Sheet

5,632,776

IMPLANTATION MATERIALS

This application is a continuation of application Ser. No. 07/867,678, filed as PCT/JP91/01609 Nov. 22, 1991, published as WO92/09312, Jun. 11, 1992, now abandoned.

TECHNICAL FIELD

The present invention relates to implantation materials excellent in anti-thrombogenic property and capable of positively introducing cells into them for preventing thrombogenesis for long periods of time, especially excellent implantation materials capable of preventing the obstruction due to thrombogenesis even when they are used as artificial small caliber blood vessels.

BACKGROUND ART

As artificial blood vessels with large and medium diameters, woven and knitted tubes of polyesters and drawn tubes made of polytetrafluoroethylene are widely clinically applied, and found to exhibit good patency even though some problems remain to be solved. However, as artificial small caliber blood vessels of less than 6 mm in inner diameter to be used for coronary bypass and peripheral arterial repair of limbs, no satisfactory products are available yet because of the obstruction due to thrombus, and autologous venous transplantation is applied. So, attempts to develop artificial small caliber blood vessels by various methods are being pursued. A major tendency in these methods is to maintain artificial anti-thrombogenic property for a long time. For example, a segmented polyurethane tube known as an anti-thrombogenic material or a material coated with a heparinized material, etc. is used. However, these materials are used with consideration given only to the maintenance of anti-thrombogenic property, and no consideration is given to the affinity with cells. So, the invasion of cells into the substrate has been little expected. Therefore, if a long period of time has passed after implantation, a tissue mainly consisting of vascular endothelial cells called pannus growing from the anastomosed portion floats partially in blood without adhering to the artificial blood vessel wall, and this suddenly obstructs the artificial blood vessel. It is known that such a case often occurs. It was reported that even artificial blood vessels prepared by drawing polytetrafluoroethylene tubes which are clinically widely used as about 6 mm artificial blood vessels caused the pannus obstruction since they were designed under the same concept.

Furthermore, for patches used for repairing hearts and large arteries, it can happen that since it takes time for the inner surface of such a patch to be covered with vascular endothelial cells, thrombus is formed on the surface and liberated to obstruct and infect peripheral blood vessels.

On the other hand, the attempt to immerse a highly porous artificial blood vessel in albumin and to autoclave it for using albumin as a covering of the artificial blood vessel can be easily used by the surgeon during an operation and can more positively inhibit the bleeding from the artificial blood vessel than the so-called pre-clotting fill the voids of an artificial blood vessel with the patient's thrombus, and so is increasingly applied.

An artificial blood vessel covered with crosslinked albumin has some anti-thrombogenic property, since the substrate covered with albumin is hydrophilic and since albumin has negative charges in the body. However, recently it has been found that if such an artificial blood vessel of 6 mm or less, especially 4 mm or less in inner diameter is implanted, the anti-thrombogenic property of the crosslinked albumin alone is insufficient to inhibit the early thrombogenesis after implantation and to maintain patency.

The artificial small caliber blood vessels of less than 6 mm in inner diameter prepared by the above mentioned methods are insufficient in anti-thrombogenic property, and also in patency because of abnormal pannus evolution. Furthermore, patches which are slow to healing and allow thrombogenesis cause peripheral blood vessels to be obstructed and infected.

The object of the present invention is to provide implantation materials which exhibit excellent patency even when used as artificial small caliber blood vessels of less than 6 mm in inner diameter.

DISCLOSURE OF THE INVENTION

The present invention is implantation materials, comprising an anti-thrombogenic material in the surface in contact with blood, of a porous substrate with its voids filled with denatured albumin or a biodegradable polyester.

Figure 1:
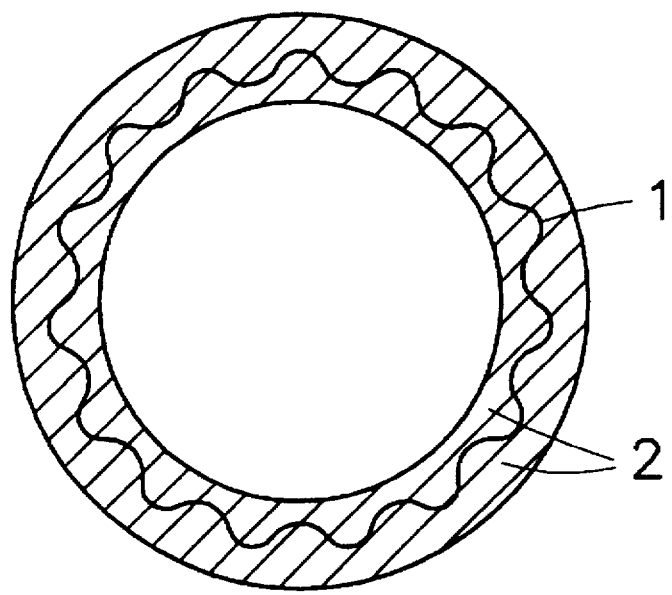
FIG. 1 is a sectional view showing a one-layer structure with an anti-thrombogenic material held by a biodegradable polymer, as a preferable embodiment where an implantation material of the present invention is used as an artificial blood vessel.

| 1 . . . substrate | 2 . . . 1st layer | 3 . . . 2nd layer |
|---|---|---|

BEST MODE FOR CARRYING OUT THE INVENTION

The implantation materials of the present invention are not especially limited as far as they are applied in the body, and concretely include artificial blood vessels and patches.

Artificial organs used at regions with blood pressure applied, like artificial blood vessels and patches are essentially required to hold strength over tens of years after implantation and may not dilate or burst like an aneurysm by blood pressure.

So, an artificial blood vessel is required to keep dynamic strength to hold its structure and to withstand blood pressure at least while the animal it is implanted in is alive.

Also in the present invention, especially in the case of using as a blood vessel or patch, at least part of the substrate must be made of a material which cannot be biodegraded and can hold its form and keep its strength to withstand blood pressure throughout the life of the animal it is implanted in.

The porous substrate can be typically a tube or sheet formed by weaving or knitting filaments or by directly processing the filaments as a nonwoven fabric.

The material of the filaments used in this case can be selected from polyesters, polyurethane, polyphenylene sulfide, polysulfones, polyethers, polyamides, polyolefins, polytetrafluoroethylene, polycarbonates, polyacetals, polyvinyl alcohol, cellulose, cellulose derivatives, etc. Filaments made of such a material can be woven, knitted or directly processed as a nonwoven fabric into a tube of 2 to 30 mm in inner diameter.

A patch can also be a sheet obtained by similarly weaving, knitting or directly processing into a nonwoven fabric, the filaments made of any material selected from those enumerated above. It is of course possible to partially cut open a tubular artificial blood vessel for use as a patch, and in this case, a patch with less thrombogenic and good healing property can be prepared.

Among the above materials, polyesters include polyethylene terephthalate, polybutylene terephthalate, polypropylene terephthalate, etc., and those with such terephthalate partially substituted by phthalate, isophthalate or any of their derivatives can also be preferably used. These polyesters are especially preferable since they are relatively stable in the body and proven to be stable after they have been used as artificial large diameter blood vessels for long periods of time.

It is especially useful that ultra fine filaments of 0.5 denier or less, preferably 0.1 denier or less account for 40 wt % or more of the filaments constituting the implantation material. That is, if ultra fine filaments cross the meshes of the woven, knitted or braided texture constituting the tube at proper intervals, like a spider web, an artificial blood vessel excellent in suturability can be prepared as stated in Japanese Patent publication No. 86-4546. Furthermore, the anti-thrombogenic property which can be given by the present invention is temporary, and so it is preferable that cells invade as early as possible. If ultra-fine filaments are used as part of the substrate, the early invasion of cells can be achieved. Especially when the artificial blood vessel is small in diameter, this property is especially important.

A tube made of polytetrafluoroethylene or polyurethane and made porous is also preferable as the substrate of the anti-thrombogenic materials of the present invention.

However, since it is known that a polyurethane tube is gradually degraded in the body, to lose its strength gradually, the polyurethane tube, if it is to be used, should be preferably reinforced by any fibrous substrate as stated above.

We maintained patency by using a method which induces the vascular endothelial cells considered to mainly provide the blood vessels with anti-thrombogenic property and cover the inner surface of the artificial blood vessel as early as possible.

Before vascular endothelial cells invade, smooth muscle cells and fibroblasts must invade the substrate on the outside.

Furthermore, it is gradually clarified that the stability of the vascular endothelial cell stratum, once formed, is maintained by the smooth muscle cells and fibroblasts which invaded on the outside (Takehisa Matsuda, Cell Technology (in Japanese), 8, 227 (1989)).

To allow the invasion of smooth muscle cells and fibroblasts into an artificial blood vessel or patch, it is essential that the substrate is a porous substance With through pores communicating from outside to inside.

An indicator for evaluating the porosity is the coefficient of water permeability (defined as the quantity (ml) of water permeating per 1 cm$^2$ in one minute at a pressure of 120 mmHg). The coefficient of water permeability required for the implantation materials should be 500 to 5000 ml/cm$^2$/min. 120 mmHg, preferably 1000 to 4000 ml/cm$^2$/min. 120 mmHg, more preferably 2000 to 3500 ml/cm$^2$/min. 120 mmHg.

However, if such a porous material is implanted, blood leaks immediately after implantation. So, to prevent it, the voids of the artificial blood vessel must be filled with any material.

In addition, the material must be gradually degraded in the body, to be replaced by cells, for not preventing the covering with vascular endothelial cells. For this reason, it is necessary to use any biodegradable polymer as described below.

The biodegradable polymer to be filled in the voids of the substrate can be denatured albumin or a biodegradable polyester.

Albumin is a protein which abundantly exists in the body as a plasma protein, and is used in a large amount also as drugs. So it is proven to be safe. If the albumin is heated, the molecules change in higher order structure and the crosslinking reaction among the molecules occur. Thus, denatured albumin insoluble in water or blood can be formed. Concretely, the artificial blood vessel is immersed in an albumin solution dissolved in any solvent and then albumin is treated to be insolubilized.

That is, in the present invention, denatured albumin which is made insoluble in water by the covalent bonding, hydrogen bonding or van der Waals force caused among albumin molecules by crosslinking treatment using heat treatment and/or a chemical crosslinking agent can be preferably used. The insolubilization treatment can substantially prevent bleeding from the artificial blood vessel.

As for the heat treatment conditions, the albumin concentration for immersion of an artificial blood vessel should be properly 5 to 50 wt %, preferably 10 to 30 wt %. If a solution with a low concentration is used, the treatment can be repeated several times, to prevent bleeding from the artificial blood vessel. The proper temperature for the heat treatment is 70° to 150° C. A preferable heat treatment method is to use hot steam for avoiding the drying of the crosslinked substance, for example, to treat at 121° C. for 5 to 40 minutes using an autoclave.

The crosslinking agent for chemical crosslinking can be preferably selected from compounds with two or more epoxy groups, isocyanate groups, aldehyde groups or active ester groups in one molecular. Furthermore, carbodiimide or Woodward's reagent K, etc. which promotes the condensation between amino groups and carboxyl groups can also be used. It is also possible to effect the reaction using a chemical crosslinking agent, together with the albumin insolubilization reaction by said heating.

The solvent for albumin used in the present invention can be preferably selected from water, ethanol/water mixture and various buffers such as phosphate buffer and tris buffer.

The biodegradable polyester can be preferably at least one or more selected from polylactic acid, polyglycolic acid, polyhydroxylactic acid, polycaprolactone, polyethylene adipate, polydioxanone and their copolymers.

The biodegradable polyester which can be used for the object should be 50000 or less, more preferably as low as less than 30000 in number average molecular weight.

The application of the biodegradable polyester can be achieved by immersing the substrate into a solution with the polymer dissolved in a solvent such as chloroform or dichloromethane, and removing the solvent by vacuum drying, etc.

In this case, the polymer concentration should be about 1 to 20%.

To make the biodegradable polyester more flexible and to improve suturability in implantation, it is especially effective to add a fatty acid or phospholipid into the polymer layer or to make it porous.

The preferable degradation period of albumin or biodegradable polyester as a biodegradable polymer used in the present invention should be 3 to 400 days, preferably 7 to 150 days when a 2 mm thick 10 mm square sheet is implanted in a rat subcutaneously.

Among denatured albumin and biodegradable polymers, denatured albumin is most preferable.

Denatured albumin or biodegradable polyester is hydrolyzed, enzymolyzed or englobed by leucocytes, and so gradually degraded, and instead, fibroblasts, smooth muscle cells and capillaries invade the substrate. Subsequently, vascular endothelial cells invade the surface in contact with blood at the anastomosed portions or from the outside, and finally the entire surface in contact with blood is covered with vascular endothelial cells.

In the present invention, filling the voids of the porous substrate with a biodegradable polymer such as denatured albumin or biodegradable polyester means to fill to such an extent that the substrate does not allow the permeation of blood, preferably to achieve 50 ml/cm$^2$/min. 120 mmHg or less as the coefficient of water permeability after filling the biodegradable polymer. If the coefficient of water permeability is obtained, it is not required to fill all the voids of the porous substrate with the biodegradable polymer, and it is only required to fill 50 to 90%, preferably 70 to 90% of the voids. Especially if the substrate is exposed on the outside, it is rather preferable for the invasion of cells. The biodegradable polymer layer as well as the substrate becomes the base to be coated with the following anti-thrombogenic material.

The anti-thrombogenic material used in the present invention is not especially limited, but can be preferably selected from the water soluble high polymers and blood anti-coagulants enumerated below.

The water soluble high polymers include glycosaminoglycans such as heparin, heparan sulfate and hyaluronic acid, polysaccharides of 200,000 or more in molecular weight, polyethylene oxide of 400 or more in molecular weight, and vinyl polymers of 250,000 or more in molecular weight [e.g., polyacrylic acid, polyvinyl alcohol, polyvinyl pyrrolidone, polyacrylamide, polyhydroxymethyl methacrylate, polysaccharides such as cellulose derivatives (carboxymethyl cellulose, hydroxyethyl cellulose and methyl cellulose), amylose, alginic acid, etc., and their copolymers and derivatives].

The blood anti-coagulants include, first of all, glycosaminoglycans such as heparin, heparan sulfate, chondroitin sulfate and hyaluronic acid also included in the water soluble high polymers. Furthermore, various low molecular compounds such as urokinase, streptokinase, hirudin, protein C, anti-thrombin III, tissue plasminogen activator, thrombomodulin, etc. and also prostaglandin E, prostacyclin and its derivatives, cyclopydine, warfarin, etc. known as antiplatelets can also be preferably used.

Among the above anti-thrombogenic materials, glycosaminoglycans can be preferably used, and especially heparin can be preferably used.

Figure 2:
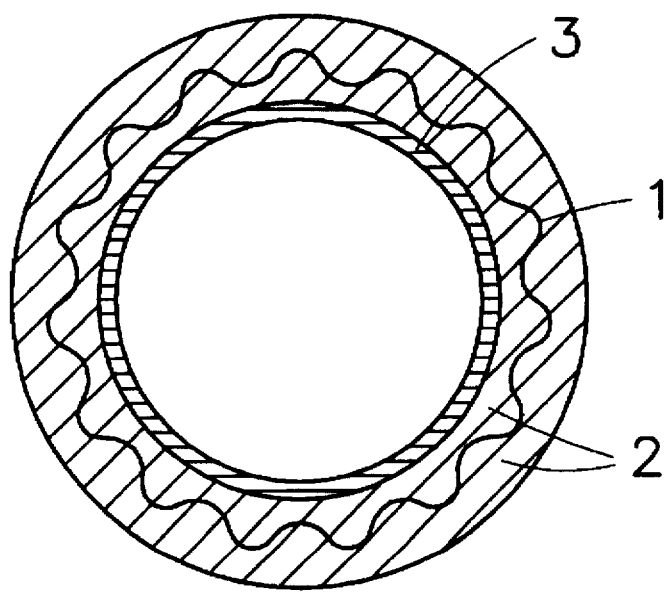
FIG. 2 is a sectional view showing a two-layer structure with an anti-thrombogenic material arranged on a biodegradable polymer, as another preferable embodiment where an implantation material of the present invention is used as an artificial blood vessel.

As shown in the drawings, an anti-thrombogenic material can be held in a biodegradable polymer (denatured albumin or biodegradable polyester) as a one-layer structure (FIG. 1), or an anti-thrombogenic material can be arranged on a biodegradable polymer as a two-layer structure (FIG. 2). Methods for preparing the respective structures are described below in detail.

[In the case of one-layer structure]

Mainly the following two methods (A) and (B) are typical methods for giving anti-thrombogenic property. In this case, since the anti-thrombogenic material applied to the substrate vanishes together with the degradation of the biodegradable polymer layer, the anti-thrombogenic material is not especially required to be biodegradable.

In this case, it is preferable that the surface in contact with blood is high in the concentration of the anti-thrombogenic material, and that the surface not in contact with blood does not substantially contain the anti-thrombogenic material.

The reason is surmised to be that even though the invasion of fibroblasts and smooth muscle cells from the side not in contact with blood must be promoted, the existence of the anti-thrombogenic material remarkably inhibits the invasion of these cells.

(A) Method of fixing at least one of anti-thrombogenic materials on the surface in contact with blood, for giving anti-thrombogenic property As the anti-thrombogenic material used, any of the above mentioned water soluble high polymers can be preferably used, and above all, heparin can be especially preferably used.

The anti-thrombogenic material can be fixed by either of the following methods when denatured albumin is used, since albumin has carboxyl groups and amino groups.

a) To use a water soluble high polymer with active ester groups, epoxy groups, aldehyde groups or isocynate groups or with such groups introduced, to cause a coupling reaction with the amino groups existing in denatured albumin.

b) To use a water soluble high polymer with amino groups, for reaction with the carboxyl groups of denatured albumin, for achieving covalent bonding by using a crosslinking agent such as water soluble carbodimide or dialdehyde.

However, the present invention is not limited to these methods. It is of course possible to use both the functional groups.

When a biodegradable polyester is used, it is possible to introduce functional groups such as amino groups or carboxyl groups into the biodegradable polyester layer, for giving a water soluble high polymer like denatured albumin. Concretely, a basic protein such as polyamine or protamine or a synthetic polyamino acid such as poly-L-lysine is dissolved into a solvent together with a biodegradable polyester, and the solution is applied to the substrate for introducing amino groups into the polyester layer.

(B) Method of slowly releasing an anti-thrombogenic material from the biodegradable polymer layer As a typical example of this method, a case of using a glycosaminoglycan as the blood anti-coagulant is described below.

In this method, the biodegradable polymer layer is caused to contain a basic protein and/or a polypeptide, and its positive charges are used to fix the glycosaminoglycan with negative charges. The glycosaminoglycan is fixed by forming an ion complex with the basic protein, and is slowly released after implantation in the blood vessel. Therefore, thrombogenesis on the surface of the material is inhibited.

A concrete method of preparation is described below in reference to a case of using denatured albumin. A solution containing albumin and a basic protein and/or a polypeptide is prepared, and the substrate is impregnated with the solution or coated with the solution on the surface in contact with blood, and heated or crosslinked as described above, to convert albumin into solid phase, thereby fixing the basic protein and/or polypeptide. Then, it is impregnated or coated with a solution containing a glycosaminoglycan on the surface in contact with blood, to form an ion complex.

In view of the safety of the body, the basic protein which can be preferably used in this method is protamine sulfate or histone, etc., and the polypeptide is poly-L-lysine or poly-L-arginine, etc. It is also possible to use both simultaneously.

The amount of the basic protein or polypeptide added should be 2 to 20 wt %, preferably 5 to 15 wt % based on the weight of albumin or biodegradable polyester. Also when both are used as a mixture, the total amount should be preferably in the above range.

The concentration of the glycosaminoglycan used should be 1 to 50 wt %, preferably 10 to 30 wt %, and the solvent can be selected from water and various buffers.

In the case of an artificial small caliber blood vessel of 4 mm or less in inner diameter, since thrombogenesis is liable to occur on the surface of the material at the time of implantation, the method (B) which positively inhibits thrombogenesis is preferable.

On the other hand, in the region which is not required to be so highly anti-thrombogenic, like an artificial blood vessel of 6 to 8 mm in patch inner diameter, the method (B) which does not inhibit the invasion of smooth muscle cells and fibroblasts by any anti-thrombogenic material can be preferably used.

<In the case of two-layer structure>

If the anti-thrombogenic material forms a second layer separately from a first layer, especially good results can be obtained. The reasons can be as stated below:

1) The inside surface can be kept more smooth.
2) Both can be made different in the degradation period of time.

Especially if the degradation of the second layer (anti-thrombogenic layer) is made lower than that of the first layer (degradable polymer layer of denatured albumin, etc.), cells can invade to the central portion of the substrate with the anti-thrombogenic property maintained, and by the time when the first layer has been degraded, smooth muscle cells and fibroblasts invade immediately below the second layer. So, since the vascular endothelial cells growing from the anastomosed portions are supported by these cells, stable and prompt covering with the endothelial cells can be achieved.

3) The release of the anti-thrombogenic material from outside can be more positively prevented.

Especially a glycosaminoglycan such as heparin or anti-platelet has excellent anti-thrombogenic property and is known to inhibit the invasion of cells such as fibroblasts. So, if the release of the glycosaminoglycan from outside is positively prevented, the invasion of cells is not inhibited.

For this purpose, it is not preferable that the first layer contains a large amount, say, 70% or more, of water.

The polymer forming the second layer (anti-thrombogenic material layer) must be biodegradable, and can be selected, for example, from polylactic acid, lactic acid-glycolic acid copolymer, poly-β-hydroxybutyric acid, polyesters such as polyorthoester and poly-e-caprolactone, poly(ethylene propylene carbonate), etc. It is especially useful that the polymer forming the second layer is a hydrogel with anti-thrombogenic property.

In this case, the gel means a high polymer with three-dimensional network structure insoluble in any solvent, or its swollen product. If a linear or branched high polymer is put into a good solvent, it is gradually swollen and finally dissolved, but it is known that a crosslinked high polymer with three-dimensional network structure is limited in swelling because of the crosslinked structure, even though it is swollen to some extent due to interaction with the solvent. In the present invention, a hydrogel using water as said solvent can be preferably used.

The hydrogel preferably used in the present invention can be preferably selected from synthetic high polymers, for example, gelatin, crosslinked gelatin, crosslinked water soluble cellulose derivatives such as ethyl cellulose, hydroxyethyl cellulose and methyl cellulose, polysaccharides such as alginic acid, agarose and carageenan, crosslinked polyethylene oxide, polyvinyl alcohol and ethylene oxide-propylene oxide block copolymer.

If the water content is too low, the anti-thrombogenic property of the hydrogel itself is too low, and if too high, a gel with a moderate strength cannot be obtained. So, the water content should be 10 to 90%, preferably 20 to 70%.

If the polymer constituting the second layer is biodegradable and anti-thrombogenic, it is not required to add an anti-thrombogenic material further to the polymer.

Among the above hydrogels, gelatin can be used most preferably since it has the following properties:

① Gelatin can be used safely in the body, and is proven as a covering material for artificial blood vessels.
② Separation between the first and second layers is hard to occur, since its adhesiveness to the first layer is high.
③ The degradation period of time can be controlled by changing the crosslinking degree of gelatin.
④ If the concentration of the solution is changed, the substrate can be easily arranged to have desired heparin slow releasability.

The gelatin layer must be crosslinked by any proper method, since it is gradually dissolved out at the body's temperature. For crosslinking, the substrate coated with the first and second layers is immersed in a solution containing a crosslinking agent.

The crosslinking agent for the gelatin layer can be selected from ethylene glycol diglycidyl ether, polyethylene glycol diglycidyl ether, glycerol polyglycidyl ether, diglycerol polyglycidyl ether, polyglycerol polyglycidyl ether, polyethylene glycol with active ester group at both the ends, glycerol with two or more active ester groups, polyglycerol, etc.

The thickness of the second layer (anti-thrombogenic layer) should be 2 to 1000 μm, preferably 20 to 500 μm. If the thickness is smaller than the range, it is difficult to give an effective anti-thrombogenic property. On the contrary, if the thickness is too large, the first and second layers are liable to be separated. The ratio of first layer:second layer in thickness should be 1:1 to 50:1, preferably 2:1 to 15:1.

In the case of a two-layer structure as described above, it is preferable that the second layer is also biodegradable. If it is not biodegradable, the obstruction by the above mentioned pannus cannot be avoided, and the obstruction in a long period of time becomes a problem.

Furthermore, in the case of a two-layer structure, it is especially important that the first and second layers are not separated. That is, the first and second layers must be strongly bonded, not to be separated even when exposed to bloodstream or even at the time of anastomosing with blood vessels.

To further ensure the bonding between both the layers, it is effective to introduce functional groups such as amino groups, carboxyl groups, hydroxyl groups or thiol groups usable for the subsequent crosslinking into both the layers, and to crosslink for bonding both the layers by covalent bonding.

As a concrete method, the following case (with denatured albumin used in the first layer and gelatin used in the second layer) is described. After covering the substrate with both the layers, it is immersed into a solution of a crosslinking agent with two or more epoxy groups, active ester groups or aldehyde groups in one molecule for crosslinking the functional groups such as amino groups, carboxyl groups or thiol groups commonly contained in both the layers, thereby achieving crosslinking between both the layers, as well as within both the layers.

As for the slow release quantity and slow release period in the case of using a glycosaminoglycan preferably used among the anti-thrombogenic materials, it is preferable to release 3 units or more on the 1st day and to release 1 unit after the 2nd day continuously, with an artificial blood vessel of 1 cm$^2$.

To realize this slow release quantity and slow release period, it is preferable to form a two-layer structure in which the second layer contains all the glycosaminoglycan and in which the glycosaminoglycan is slowly released from the second layer.

The anti-thrombogenic material content of the second layer should be 1 to 50 wt %, preferably 5 to 30 wt %, and the solvent can be water or any of various buffers.

If an anti-thrombogenic material with negative charges such as a glycosaminoglycan is used, letting the second layer contain a basic protein and/or a polypeptide as in the case of the one-layer structure also gives preferable results.

Especially when gelatin is used as the second layer, the slow releasability of heparin, one of the most preferable anti-thrombogenic materials, can be obtained by any of the following methods:

① To crosslink the gelatin layer which already contains heparin.

② To let the basic functional groups already introduced in the gelatin layer and a glycosaminoglycan form an ion complex, for allowing slow release.

Furthermore, the anti-thrombogenic property can be improved by fixing any of said anti-thrombogenic high polymers onto the second layer on the surface in contact with blood or by coating the second layer with a protein in blood such as albumin or lipoprotein.

EXAMPLES

The present invention is described below in more detail in reference to examples, but is not limited thereto or thereby.

Present Invention Example 1

Sixty weight percent of ultra fine polyester filaments (714 filaments made 50 deniers, and so one filament was 0.07 denier) and 40 wt % of 1.4-denier polyester fibers were mixed and formed into artificial blood vessels of 4 mm in inner diameter by plain weave. A thick polyester film was inserted into each of the tubes, and they were subjected to light card clothing and raising from both sides. Then, high pressure water jet was applied to intertwine filaments mutually. The artificial blood vessels were 3050 in the coefficient of water permeability (defined as the quantity (ml) of water permeating per 1 cm$^2$ in one minute at a pressure of 120 mm Hg). In each of the meshes of the texture, several separated ultra fine filaments had crossed.

Into each of the artificial blood vessels, a teflon rod with a diameter equal to the inner diameter of the artificial blood vessel was inserted, and they were immersed in 20 ml of a phosphate buffer with 3.0 g of bovine albumin dissolved, for 3 minutes, and then autoclaved at 121° C. for 15 minutes, to fix denatured albumin. This operation was repeated twice. Ten grams of gelatin derived from swine and 3.2 g of heparin were dissolved into 40 ml of distilled water at 50° C. The gelatin-heparin solution was caused to flow into the cavities of the artificial blood vessels treated by albumin, to coat the artificial blood vessels internally. They were allowed to stand at room temperature for 10 minutes, to gel the gelatin layer, and were immersed in ethanol-water mixture (80:20 (vol/vol)) containing 5% of ethylene glycol diglycidyl ether, for crosslinking treatment at 35° C. for 72 hours.

The artificial blood vessels obtained had a two-layer structure in cross section as shown in FIG. 2.

Such six artificial blood vessels were implanted into the carotid arteries of three dogs for 6 to 30 days. For implantation, the needle could well penetrate the artificial blood vessels, and anastomosability and suturability were good without any fray observed. After lapse of a predetermined time, the artificial blood vessels were taken out, and all were found to remain patent. On the inner surfaces, no thrombus was observed at all. They were observed on the 28th day after implantation by an optical microscope, and it was found that the artificial blood vessels had their albumin layer degraded at the central portion, with many fibroblasts and leucocytes observed. At the anastomosed portions, the albumin and gelatin layers had been perfectly degraded, and instead, many fibroblasts were observed. Furthermore, the inner surfaces at the anastomosed portions were observed to be covered with vascular endothelial cells growing from host blood vessels.

Sheets of 2 mm thick×10 mm square made of denatured albumin only were prepared without using the polyester substrate and implanted subcutaneously in rats. About 60 days later, they were observed to have been perfectly degraded and replaced by connective tissue.

Present Invention Example 2

Artificial blood vessels of 4 mm in inner diameter were formed using ultra fine polyester filaments as done in Present Invention Example 1. Two grams of human albumin and 0.3 g of poly-L-lysine were dissolved into 10 ml of physiological salt solution, and the artificial blood vessels were immersed in the solution for 10 minutes as done in Present Invention Example 1, and then autoclaved at 121° C. for 15 minutes, to fix and denature albumin. This operation was repeated twice.

In the cavities of the artificial blood vessels, 10% heparin aqueous solution was circulated at 45° C. for 120 minutes, to fix heparin.

The artificial blood vessels obtained had a one-layer structure in cross section as shown in FIG. 1.

Eight such artificial blood vessels were implanted into the carotid arteries of four dogs for 25 to 30 days. Among the 8 vessels, 4 vessels remained patent, and one was obstructed, which had an infection complication. They were observed by an optical microscope, and it was found that the composition had been mostly absorbed and many fibroblasts and capillaries were observed in the walls of the artificial blood vessels. Not only at the anastomosed portions but also in the central portions of the artificial blood vessels, colonies of endothelial cells were observed, to partially cover the inner surfaces of the artificial blood vessels.

Sheets of 2 mm thick×10 mm square made of L-lysine-containing denatured albumin were prepared, without using the polyester substrate, and implanted subcutaneously in rats. About 60 days later, they were observed to have been perfectly degraded and replaced by connective tissue.

Comparative Example 1

The same artificial blood vessels as used in Present Invention Example 1 were used, to prepare tubes covered with denatured albumin only as done in Present Invention Example 1. They were implanted as done in Present Invention Example 2. Among eight vessels, one only remained patent.

Comparative Example 2

Artificial blood vessels were prepared as done in Present Invention Example 1, except that heparin was not contained in the gelatin layer, and implanted. Among eight vessels, one only remained patent.

Present Invention Example 3

Sixty weight percent of ultra fine polyester filaments (714 filaments made 50 deniers, and so 1 filament was 0.07 denier) and 40 wt % of 1.4-denier polyester filaments were mixed and formed into 10×10 cm patches by plain weave. Into each of the tubes, a thick polyester film was inserted, and they were subjected to light card clothing and raising from both sides. Then, high pressure water jet was applied to intertwine the filaments mutually. The artificial blood vessels were 2500 in the coefficient of water permeability (defined as the quantity (ml) of water permeating per 1 cm$^2$ in one minute at a pressure of 120 mm Hg). In each of the meshes of the texture, several divided ultra fine filaments had crossed.

The patches were immersed in 20 ml of a phosphate buffer with 3.0 g bovine albumin (fraction V) dissolved, for 3 minutes, and then autoclaved at 121° C. for 15 minutes, to fix albumin. This operation was repeated twice.

Subsequently, 10 g of gelatin derived from swine and 1.0 g of protamine sulfate were dissolved into 40 ml of distilled water at 50° C. The gelatin-protamine solution was applied to the albumin-treated patches on one side. They were allowed to stand at room temperature for 10 minutes, to gel the gelatin layer, and immersed in ethanol-water mixture (80:20 (vol/vol)) containing 1% of ethylene glycol diglycidyl ether and 1.0 wt % of water soluble carbodiimide, for crosslinking treatment at 35° C. for 78 hours. The patches obtained had a two-layer structure in cross section as shown in FIG. 2.

The patches were trimmed into 2×3 cm pieces. One of them was sutured to the region from the outlet canal of the right ventricle to the pulmonary artery of a mongrel dog. On the 40th day after implantation, the inner surface of the substrate showed little thrombus. A tissue sample was observed by an optical microscope, and it was found that albumin had been mostly absorbed and that the inside wall was covered with cells like endothelial cells.

Sheets of 2 mm thick×10 mm square made of denatured albumin were prepared without using the polyester substrate, and implanted subcutaneously in rats. About 60 days later, they were observed to have been perfectly degraded and replaced by connective tissue.

Comparative Example 3

A marketed polyester patch not filled with denatured albumin (Cooly Low Porosity produced by Meadox) was examined as done in Present Invention Example 3. The inside surface was mostly covered with red thrombus, and cells like endothelial cells were not observed at all.

Present Invention Example 4

The polyester tubes used in Present Invention Example 1 were immersed into a chloroform solution containing 2 wt % of L-lactic acid-glycolic acid copolymer (70:30 (mol/mol)) of 3500 in number average molecular weight, and dried by blast. This operation was repeated three times, and the coefficient of water permeability could be made almost zero.

Through the cavities, 3% hydroxyethyl cellulose aqueous solution was fed three times, for coating, and they were immersed in ethanol-water mixture (80:20 (vol/vol)) containing 5% of ethylene glycol diglycidyl ether. With pH adjusted to 9, they were treated at 45° C. for 48 hours for crosslinking. The artificial blood vessels obtained had a two-layer structure as shown in FIG. 2.

Six such artificial blood vessels were implanted in the carotid arteries of three dogs for 100 days. At the time of implantation, the needle well penetrated the artificial blood vessels, and the anastomosability and suturability were good without any fray observed. After lapse of predetermined time, the artificial blood vessels were taken out and all were found to be patent.

Sheets of 2 mm thick×10 mm square made of L-lactic acid-glycolic acid copolymer were prepared without using the polyester substrate, and implanted subcutaneously in rats. About 60 days later, they were found to have been perfectly degraded and replaced by connective tissue.

Comparative Example 4

The artificial blood vessels of Present Invention Example 4 were used and implanted similarly without the coating of hydroxyethyl cellulose. All the four vessels were found to be obstructed.

INDUSTRIAL APPLICABILITY

As described above, the implantation materials of the present invention are excellent in anti-thrombogenic property and prevent the anti-thrombogenesis for long periods of time by positively introducing cells into the implantation materials. They especially show usefully excellent patency as artificial small diameter blood vessels.

We claim:

1. An anti-thrombogenic implantation material consisting essentially of a layer of a porous substrate made of individual fibers having voids filled with a biodegradable polymer and a layer of an anti-thrombogenic agent formed onto a surface portion formed by said substrate and said biodegradable polymer, wherein said porous substrate has a coefficient of water permeability of 500 to 5,000 ml/cm$^2$/min. 120 mmHg and said biodegradable polymer has a degradation period that is shorter than that of said anti-thrombogenic agent of said layer.

2. An anti-thrombogenic implantation material according to claim 1, wherein said biodegradable polymer is a biodegradable polyester.

3. An anti-thrombogenic implantation material according to claim 2, wherein the biodegradable polyester is selected from the group consisting of polylactic acid, polyglycolic acid, polyhydroxylactic acid, polycaprolactone, polyethylene adipate, polydioxanone and copolymers of the foregoing.

4. An anti-thrombogenic implantation material according to claim 1, wherein said biodegradable polymer is denatured albumin.

5. An anti-thrombogenic implantation material according to claim 4, wherein said denatured albumin is crosslinked by a treatment selected from the group consisting of heat treatment, chemical crosslinking agent and a combination of heat treatment and a chemical crosslinking agent.

6. An anti-thrombogenic implantation material according to claim 1, wherein an additive selected from the group consisting of a basic protein, a polypeptide and both of a basic protein and a polypeptide is added to the biodegradable polymer.

7. An anti-thrombogenic implantation material according to claim 1, wherein an additive selected from the group consisting of a basic protein, a polypeptide and both of a basic protein and a polypeptide is added to the anti-thrombogenic agent layer.

8. An anti-thrombogenic implanation material according to claim 1, wherein the degradation period of the biogradable polymer is 3 to 400 days when said material is a sheet 10 mm square×2 mm thick and implanted subcutaneously in a rat.

9. An anti-thrombogenic implantation material according to claim 1, wherein the porous substrate contains at least 40 wt % of 0.5 denier or less.

10. An anti-thrombogenic implantation material according to claim 1, wherein the anti-thrombogenic agent is selected from the group consisting of a water soluble high polymer, both of a water soluble high polymer and a blood coagulant.

11. An anti-thrombogenic implantation material according to claim 1, wherein the anti-thrombogenic agent is a glycosaminoglycan.

12. An anti-thrombogenic implantation material according to claim 1, comprising a structure selected from the group consisting of artificial blood vessels and patches.

13. The anti-thromogenic implantation material defined in claim 1 wherein said voids are filled to such an extent that said substrate does not allow permeation of blood and achieves a coefficient of water permeability after filling with said biodegradable polymer of 50 ml/cm$^2$/min. 120 mmHg or less.

14. An anti-thrombogenic implanation material according to claim 1 wherein the porous substrate is formed by a method selected from the group consisting of weaving and knitting.

15. An anti-thrombogenic implantation material according to claim 1 wherein the porous substrate is formed into a non-woven fabric by processing filaments.

* * * * *

UNITED STATES PATENT AND TRADEMARK OFFICE
CERTIFICATE OF CORRECTION

PATENT NO. : 5,632,776
DATED : May 27, 1997
INVENTOR(S) : Hajimu Kurumatani, et al It is certified that error appears in the above-indentified patent and that said Letters Patent is hereby corrected as shown below:

Column 13, line 11, after "of", please insert —fibers of—.

Column 13, line 15, before "both", please insert —a blood anticoagulant, and—.

Column 13, line 16, "coagulant" should read —anticoagulant—.

Signed and Sealed this

Twenty-third Day of September, 1997

*Attest:*

BRUCE LEHMAN

*Attesting Officer*  *Commissioner of Patents and Trademarks*